United States Patent [19]

Boden

[11] 4,315,911

[45] Feb. 16, 1982

[54] FLAVORING WITH MIXTURE OF ACETYL DIISOBUTYLENES

[75] Inventor: Richard M. Boden, Monmouth Beach, N.J.

[73] Assignee: International Flavors & Fragrances Inc., New York, N.Y.

[21] Appl. No.: 195,672

[22] Filed: Oct. 9, 1980

[51] Int. Cl.³ .............................................. A23L 1/226
[52] U.S. Cl. ........................................ 424/48; 424/49; 424/54; 424/358; 426/3; 426/534; 568/417
[58] Field of Search ...................... 426/3, 534; 424/49, 424/54, 358, 48; 568/417

[56] References Cited

U.S. PATENT DOCUMENTS

| | | | |
|---|---|---|---|
| 2,315,046 | 3/1943 | Byrns | 568/319 |
| 2,870,210 | 1/1959 | Surmatis | 426/534 X |
| 3,453,317 | 7/1969 | Marbet | 252/522 R X |
| 3,928,402 | 12/1975 | Näf | 568/417 X |
| 4,234,518 | 11/1980 | Yoshida et al. | 426/534 X |

*Primary Examiner*—Joseph M. Golian
*Attorney, Agent, or Firm*—Arthur L. Liberman

[57] ABSTRACT

Described for augmenting or enhancing the aroma or taste of foodstuffs, chewing gums, toothpastes and medicinal products are certain branched ketones having the generic structure:

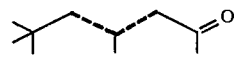

wherein one of the dashed lines is a carbon-carbon double bond and the other of the dashed lines represents a carbon-carbon single bond.

7 Claims, 6 Drawing Figures

FIG.1
GLC PROFILE FOR FRACTION 2 OF EXAMPLE I.

FIG.2

GLC PROFILE FOR FRACTION 9 OF EXAMPLE I.

FIG. 4
NMR SPECTRUM FOR EXAMPLE I, PEAK 2 OF GLC PROFILE OF FIG. 2.

FIG. 5

IR SPECTRUM FOR EXAMPLE I, PEAK I OF GLC PROFILE OF FIG. 2.

FLAVORING WITH MIXTURE OF ACETYL DIISOBUTYLENES

BACKGROUND OF THE INVENTION

The present invention relates to branched ketones of the genus of compounds having the structure:

wherein one of the dashed lines is a carbon-carbon double bond and the other of the dashed lines represents a carbon-carbon single bond, and to novel compositions using one or both of such branched ketones to augment or enhance the flavor and/or aroma of consumable materials, or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Sweet, spicy, minty, herbaceous, bread-like, caraway-like and dill-like aroma and taste nuances are particularly desirable for use in foodstuff flavors, chewing gum flavors, toothpaste flavors and medicinal product flavors.

Unsaturated ketones including unsaturated branched aliphatic, acyclic ketones are well known for use in augmenting or enhancing the aroma and/or taste of consumable materials. Thus, Arctander, "Perfume & Flavor Chemicals (Aroma Chemicals)", published 1969, discloses at monograph No. 472, the use of butylidene acetone having the structure:

Arctander states that butylidene acetone has a powerful, grassy, green pungent odor and a rather poor tenacity. At monograph 2427, Vol. 2 Arctander states that Octylidene acetone having the structure:

is useful in Jasmin compositions as a modifier for Amylcinnamic aldehyde, or in Gardenia and other heavy floral perfumes, where herbaceous-fruity notes are desirable and compatible with the fragrance picture.

U.S. Pat. No. 2,315,046 discloses the use as ingredients in perfumery of certain acylated olefins, which olefins have structures such as:

These materials are prepared interalia from commercial diisobutylene according to the reaction:

wherein n is 3 or more, and R represents a hydrocarbon radical. Branched unsaturated alpha-beta ketones were known prior to that, for example in U.S. Pat. No. 2,246,032, issued on June 17, 1941, disclosing compounds having the generic structure:

wherein $R_1$-$R_7$ may be any member of a group consisting of hydrogen, aliphatic and cyclo praffinic.

Also, claimed in U.S. Pat. No. 2,315,046 are compounds having the structure:

In addition, U.S. Pat. No. 2,463,742 discloses the reaction:

U.S. Pat. No. 3,453,317, issued on July 1, 1969, discloses certain gamma, delta unsaturated ketones as odorants for perfumery purposes at Column 4, line 33 including the group of ketones having the structure:

wherein R₁-R₅ are various hydrocarbon radicals.

U.S. Pat. No. 2,870,210, discloses as having aromas such as fruity, "reminiscent of apple juice" the compound 6,8-dimethyl-5-nonene-2-one having the structure:

as well as 6,10-dimethyl-5-undecane-2-one having the structure:

Nothing in the prior art specifically discloses the use of the genus of compounds having the structure:

wherein one of the dashed lines represents a carbon-carbon double bond and the other of the dashed lines represents a carbon-carbon single bond for augmenting or enhancing the aroma or taste of foodstuffs, chewing gums, toothpastes or medicinal products.

THE INVENTION

It has now been discovered that novel solid and liquid foodstuff, chewing gum, medicinal product and toothpaste compositions and flavoring compositions therefor having sweet, spicy, minty, herbaceous, bread-like, caraway-like and dill-like aroma and taste nuances may be provided by the utilization of one or both of the unsaturated branched ketones having the structures:

or defined according to the genus:

wherein one of the dashed lines represents a carbon-carbon double bond and the other of the dashed lines represents a carbon-carbon single bond.

The compounds having the structures:

and may be obtained by first dimerizing isobutylene according to the teachings of U.S. Pat. No. 2,315,046 or according to the teaching of Japanese Kokai No. 79,157,510 published on Dec. 12, 1979 (abstracted in Chem Abstracts Volume 93:25885a) wherein the dimerization of isobutylene is indicated to take place in the presence of alkylaluminum chloride catalysts such as ethyl aluminum dichloride.

The resulting mixture of dimers of isobutylene may be separated or may be used as is in the next reaction wherein the dimer or mixture of dimers is acylated with either acetic anhydride or acetyl chloride or acetyl bromide in the presence of a catalyst such as boron trifluoride, boron trifluoride etherate, stannic chloride, ethyl aluminum dichloride or diethyl aluminum chloride according to, for example, the reaction:

The conditions of the acylation are also taught in U.S. Pat. No. 2,315,046 as well as in U.S. Pat. No. 2,246,032.

When the unsaturated branched ketones of our invention are used as food flavor adjuvants or medicinal product flavor adjuvants or toothpaste flavor adjuvants or chewing gum flavor adjuvants, the nature of the co-ingredients included with each of the said unsaturated branched ketones of our invention in formulating the product composition will also serve to augment or enhance the organoleptic characteristics of the ultimate foodstuff, chewing gum, medicinal product or toothpaste treated therewith.

The term "augment" in its various forms is used herein to mean the supplying, modifying or imparting of a flavor or aroma characteristic, note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

As used herein, the term "foodstuff" includes both solid and liquid ingestible materials which usually do, but need not, have nutritional value. Thus, foodstuffs includes soups, convenience foods, beverages, dairy products, candies, vegetables, cereals, soft drinks, snacks and the like.

As used herein, the term "medicinal products" includes both solids and liquids which are ingestible non-toxic materials which have medicinal value such as cough syrups, cough drops, aspirin and chewable medicinal tablets.

The term "chewing gum" is intended herein to be a foodstuff which is a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the unsaturated branched ketones of our invention, and, in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is required that any such material be "ingestibly acceptable", and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthically pleasing aroma and taste profile. Such materials, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiarybutyl-4-methyl phenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl cellulose and methyl cellulose; natural and synthetic gums such as gum arabic, gum tragacanth; gelatin, proteinaceous materials, lipids; carbohydrates, starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as, palmitic acid, myristic acid and the like, mono- and diglycerides of fatty acids, lecithin, defoaming and flavor-dispersing agents such as sorbitan monostearate, potassium monostearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric, curcumin and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, 2-methyl-cis-3-pentenoic acid; ketones and aldehydes, e.g., octanal, n-decanal, acetaldehyde, acetophenone, acetone, acetyl methyl carbinol, acrolein, n-butanal, crotonal, diacetyl, 2-methyl butanal, beta, beta-dimethyl-acrolein, methyl-n-amyl ketone, n-hexanal, 2-hexenal, isopentanal, hydrocinnamic aldehyde, cis-3-hexenal, 2-heptenal, nonyl aldehyde, citral, 4-(p-hydroxyphenyl)-2-butanone, alpha-ionone, 2-methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, β-cyclohomocitral,. 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, fenchyl alcohol, isofenchyl alcohol, phenyl-2-ethanol, α-terpineol, cis-trpineol hydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl α-methylbutyrate, ethyl propionate, ethyl salicylate, trans-2-hexenyl acetate, hexyl acetate, 2-hexenyl butyrate, hexyl butyrate, isoamyl acetate, isopropyl butyrate, dimethyanthranilate, methyl acetate, methyl butyrate, methyl caproate, methyl isobutyrate, α-methylphenylglycidate, ethyl succinate, isobutyl cinnamate, cinnamyl formate, methyl cinnamate and terpinenyl acetate; hydrocarbons such as dimethyl naphthalene, dodecane, methyl diphenyl, methyl naphthalene, myrcene, cadinene, limonene, naphthalene, octadecane, tetradecane, tetramethyl naphthalene, tridecane, trimethyl naphthalene, undecane, caryophyllene, 1-phellandrene, p-cymene, 1-α-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, α-methyl-3-ethylpyrazine, tetramethylpyrazine, trimethylpyrazine; essential oils, such as jasmine absolute, cassia oil, cinnamon bark oil, rose absolute, orris absolute, lemon essential oil, orange essential oil, grapefruit essential oil, Bulgarian rose, oil of dill, oil of caraway, oil of spearmint, yara yara and vanila; lactones such as gammanonalactone; sulfides, e.g., methyl sulfide and other materials such as maltol, and acetals (e.g., 1,1-diethoxyethane, 1,1-dimethoxyethane and dimethoxymethane).

The specific flavoring adjuvants selected for use may be either solid or liquid depending upon the desired physical form of the ultimate product, i.e., foodstuff, whether simulated or natural, and should, in any event, (i) be organoleptically compatible with the unsaturated branched ketones of our invention by not covering or spoiling the organoleptic properties (aroma and/or taste) thereof; (ii) be non-reactive with the unsaturated branched ketones of our invention; and (iii) be capable of providing an environment in which the unsaturated branched ketones of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, augmented or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of unsaturated branched ketones of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to augment or enhance the organoleptic characteristics of the parent composition, whether foodstuff per se, chewing gum per se, medicinal product per se, toothpaste per se, or flavoring composition.

The use of insufficient quantities of unsaturated branched ketones of our invention will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of unsaturated branched ketones of our invention ranging from a small but effective amount, e.g., 0.02 parts per million (ppm) up to about 50 parts per million (ppm) based on total composition are suitable. Concentrations in excess of the maximum quantity stated are not normally recommended, since they fail to provide commensurate enhancement of organoleptic properties. In those instances, where the unsaturated branched ketones of our invention is added to the foodstuff as an integral component of a flavoring composition, it is, of course, essential that the total quantity of flavoring composition employed be sufficient to yield an effective unsaturated branched ketones of our invention concentration in the foodstuff product.

Food flavoring compositions prepared in accordance with the present invention preferably contain the unsaturated branched ketones of our invention in concentrations ranging from about 0.05% up to about 5% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the unsaturated branched ketones of our invention with, for example, gum arabic, gum tragacanth, carrageenan and the like, and thereafter spray-drying the resultant mixture whereby to obtain the particulate solid product. Pre-prepared flavor mixes in powder form, e.g., a fruit-flavored powder mixes are obtained by mixing the dried solid components, e.g., starch, sugar and the like and the unsaturated branched ketones of our invention in a dry blender until the requisite degree of uniformity is achieved.

It is presently preferred to combine with the unsaturated branched ketones of our invention, the following adjuvants:

Oil of dillweed
Oil of garlic
Oil of capsicum
Oil of cassia
Oil of cloves
Oil of pimenta berries
Oil of mustard
Oil of bay leaves
L-carvone
D-carvone
Spearmint oil
Cumin aldehyde The following examples are intended to illustrate the instant invention. It wil be understood that these examples are illustrative and that the invention is to be considered restricted thereto only as indicated in the appended claims.

All parts and percentages given herein are by weight unless otherwise specified.

EXAMPLE I

Preparation of Acetyl Diisobutylene Reaction

Into a five liter, three-neck reaction vessel equipped with stirrer, thermometer, reflux condenser, heating mantle and addition funnel is placed 1,300 grams of acetic anhydride and 195 grams of boron trifluoride etherate. The resulting mixture is heated to a temperature of 80°–85° C. At this point 690 grams of diisobutylene being a mixture of compounds having the structures:

is added dropwise while maintaining the reaction temperature at 80°–82° C., over a period of one hour. At the end of the one hour period, the reaction mass is continued to be stirred and maintained at 83° C. At the end of 3.5 hours, the reaction mass is cooled and poured into one liter of water. The reaction mass is then washed as follows:

(a) Two one-liter water portions
(b) Two one-liter 10% aqueous sodium hydroxide portions
(c) Two one-liter saturated sodium chloride portions The reaction mass is now at a pH of 7. The reaction mass is dried and stripped of solvent using a crude oil weighing 620 grams. The reaction mass is then distilled on a 1' Goodloe column at reflux ratios of between 9:1 and 4:1 yielding the following fractions:

| Fraction No. | Vapor Temp. °C. | Liquid Temp. °C. | Head Vacuum mm. Hg | Reflux Ratio R/D | Weight of Fraction |
|---|---|---|---|---|---|
| 1 | 43/50 | | 3.0/3.0 | 9:1 | 39 |
| 2 | 50 | 59 | 2.0 | 9:1 | 40 |
| 3 | 50 | 60 | 2.0 | 9:1 | 43 |
| 4 | 51 | 60 | 2.0 | 9:1 | 35 |
| 5 | 52 | 61 | 2.0 | 9:1 | 42 |
| 6 | 52 | 63 | 2.0 | 9:1 | 43 |
| 7 | 53 | 63 | 2.0 | 4:1 | 43 |
| 8 | 53 | 63 | 2.0 | 4:1 | 44 |
| 9 | 53 | 65 | 2.0 | 9:1 | 41 |
| 10 | 53 | 81 | 2.0 | 9:1 | 39 |
| 11 | 53 | 223 | 2.0 | 9:1 | 19 |

The reaction product is determined by GLC, NMR and mass spectra analyses to contain compounds having the structures:

and

Figure 1:
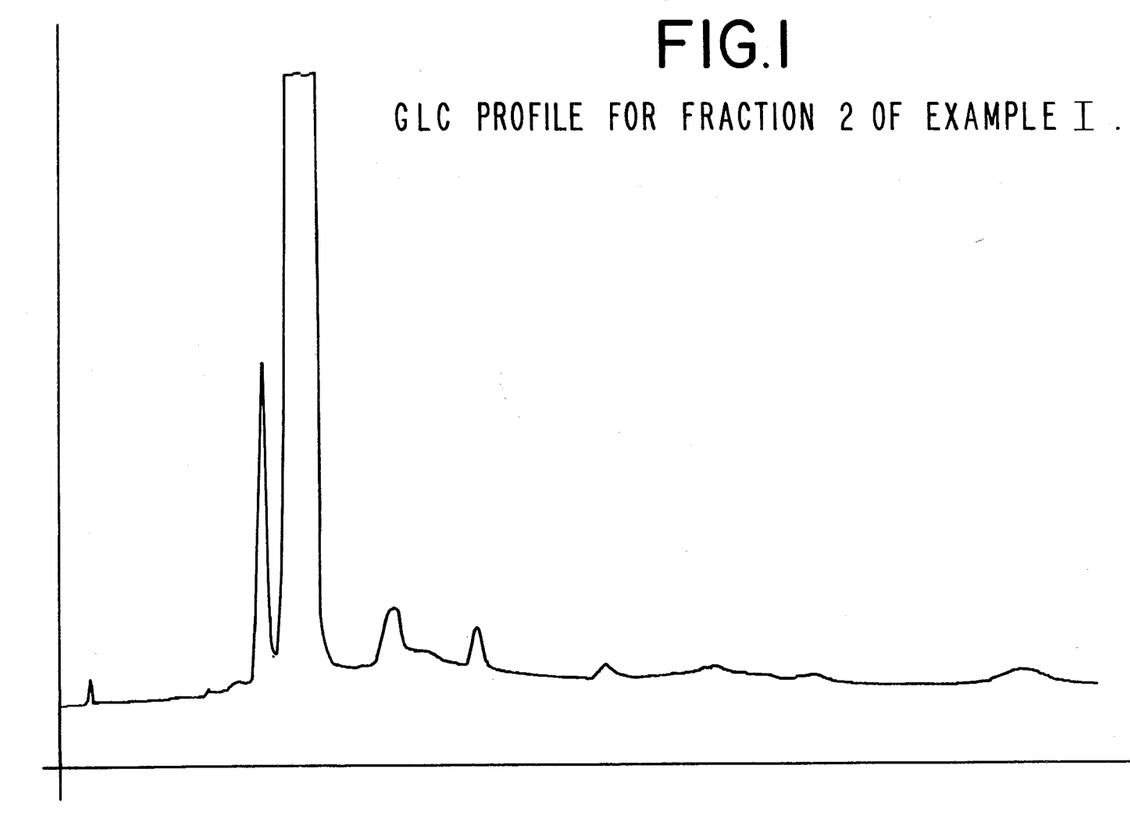
FIG. 1 is the GLC profile for distillation fraction 2 of the reaction product of Example I containing the compounds having the structures.

FIG. 1 is the GLC profile for distillation fraction 2 of the reaction product of Example I containing the compounds having the structures:

and

Figure 2:
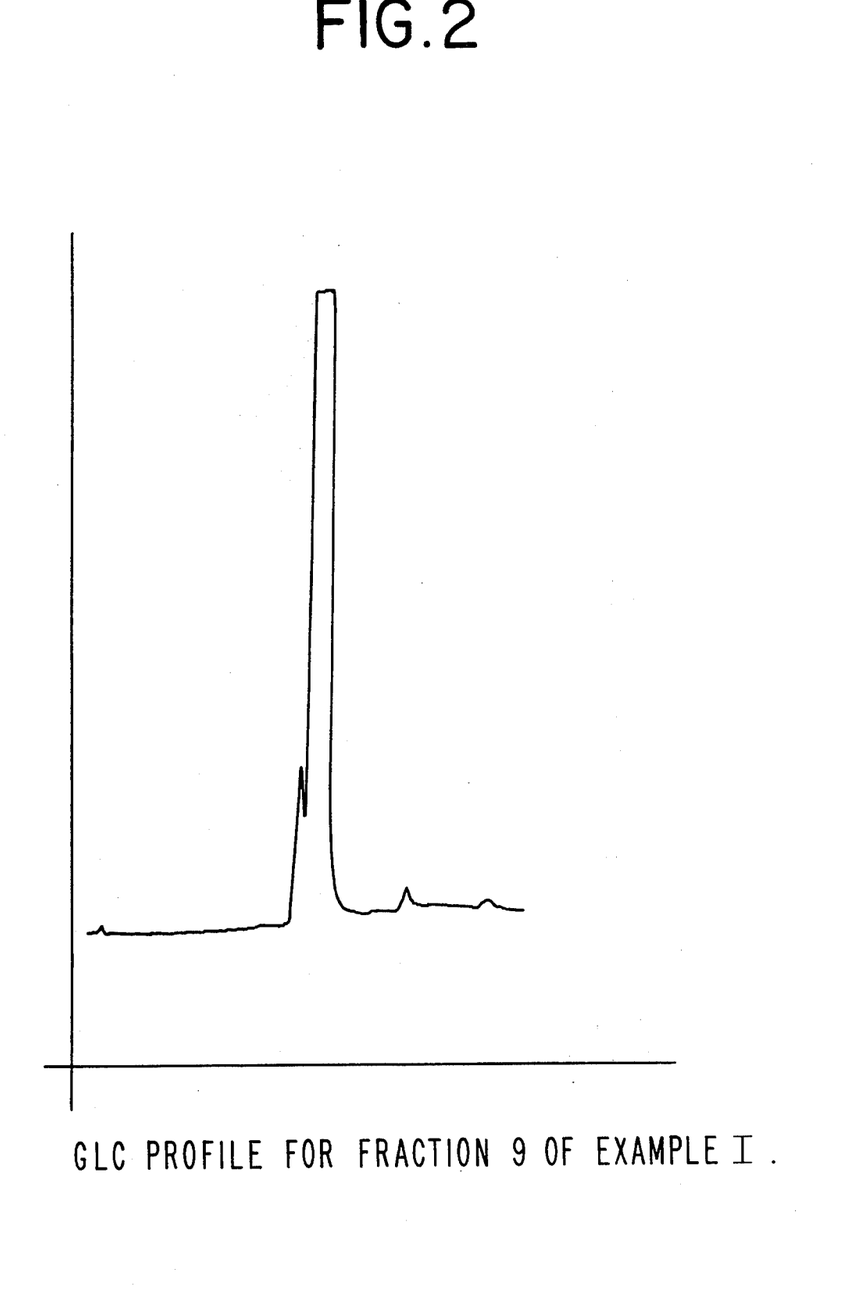
FIG. 2 is the GLC profile for distillation fraction 9 of the reaction product of Example I containing the compounds having the structures.

FIG. 2 is the GLC profile for distillation fraction 9 of the reaction product of Example I containing the compounds having the structures:

and

Figure 3:
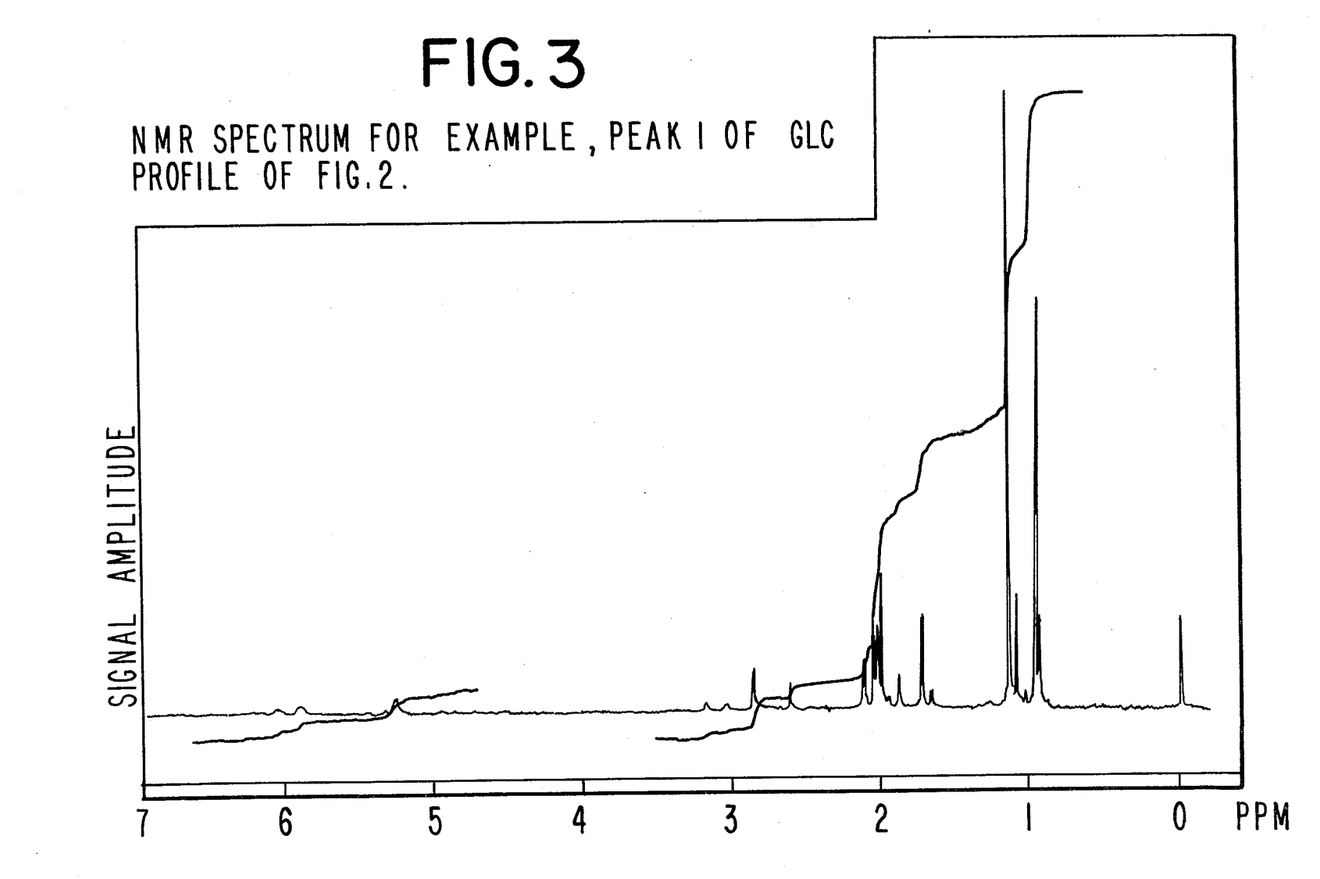
FIG. 3 is the NMR spectrum for peak 1 of the GLC profile of FIG. 2 containing the compounds having the structures.

FIG. 3 is the NMR spectrum for peak 1 of the GLC profile of FIG. 2 containing the compounds having the structures:

and

Figure 4:
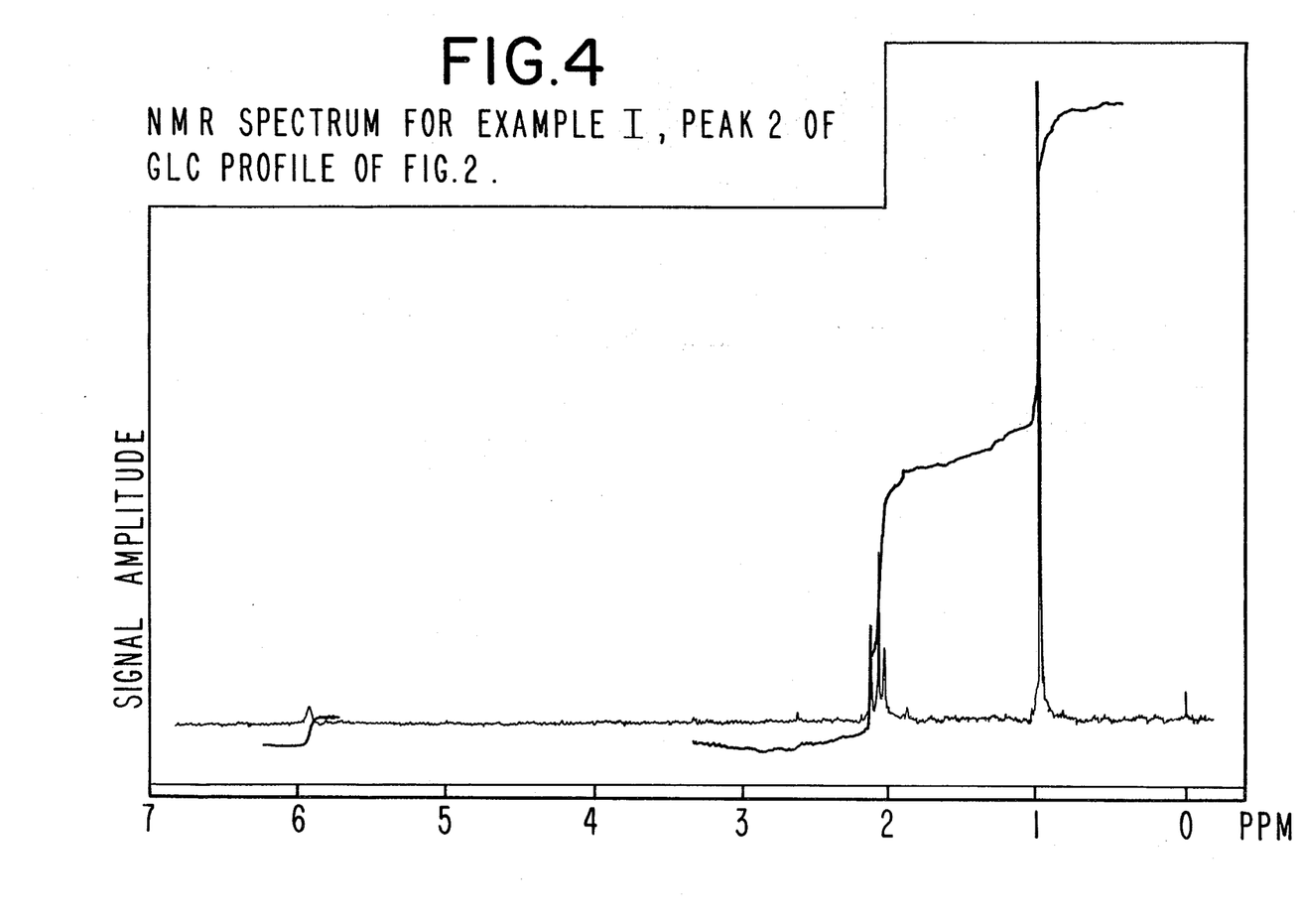
FIG. 4 is the NMR spectrum for peak 2 of the GLC profile of FIG. 2 containing the compounds having the structures.

FIG. 4 is the NMR spectrum for peak 2 of the GLC profile of FIG. 2 containing the compounds having the structures:

and

Figure 5:
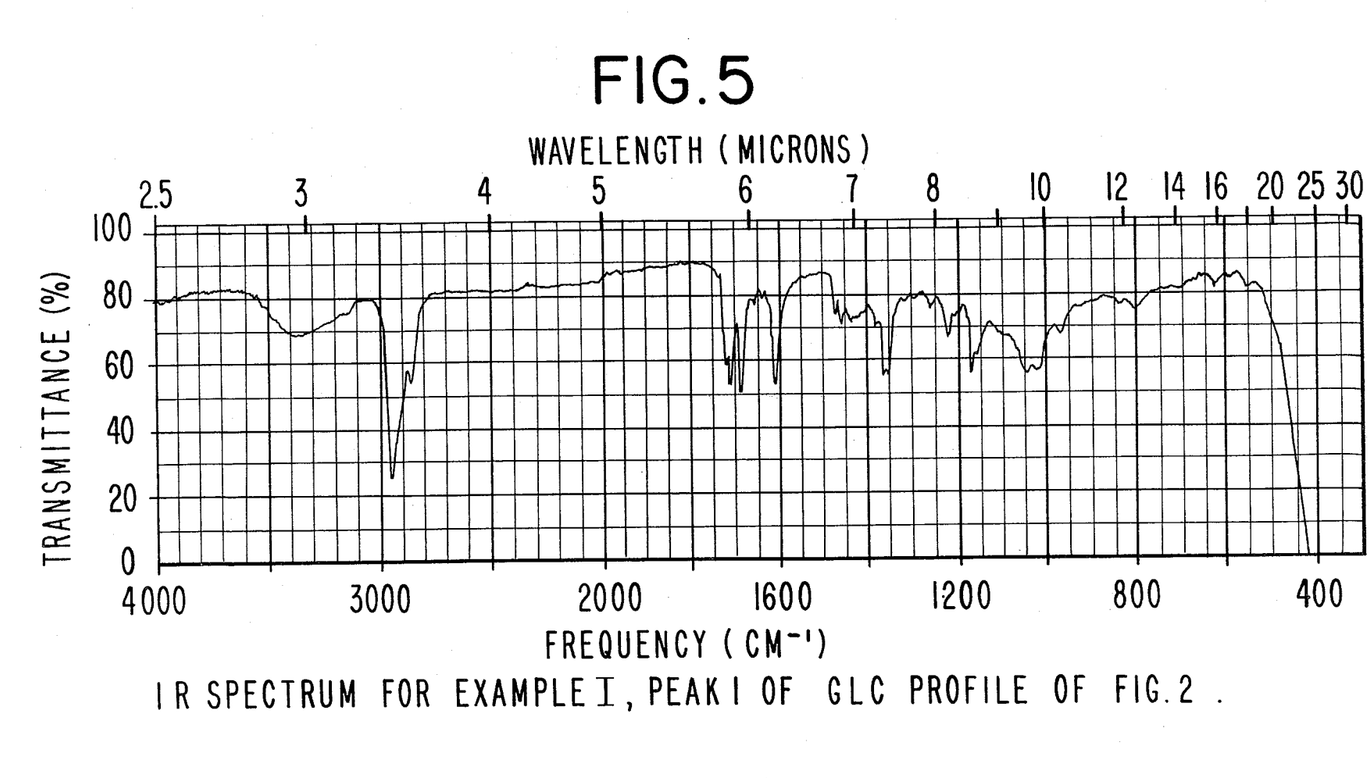
FIG. 5 is the infra-red spectrum for peak 1 of the GLC profile of FIG. 2 containing the compounds having the structures.

FIG. 5 is the infra-red spectrum for peak 1 of the GLC profile of FIG. 2 containing the compounds having the structures:

and

Figure 6:
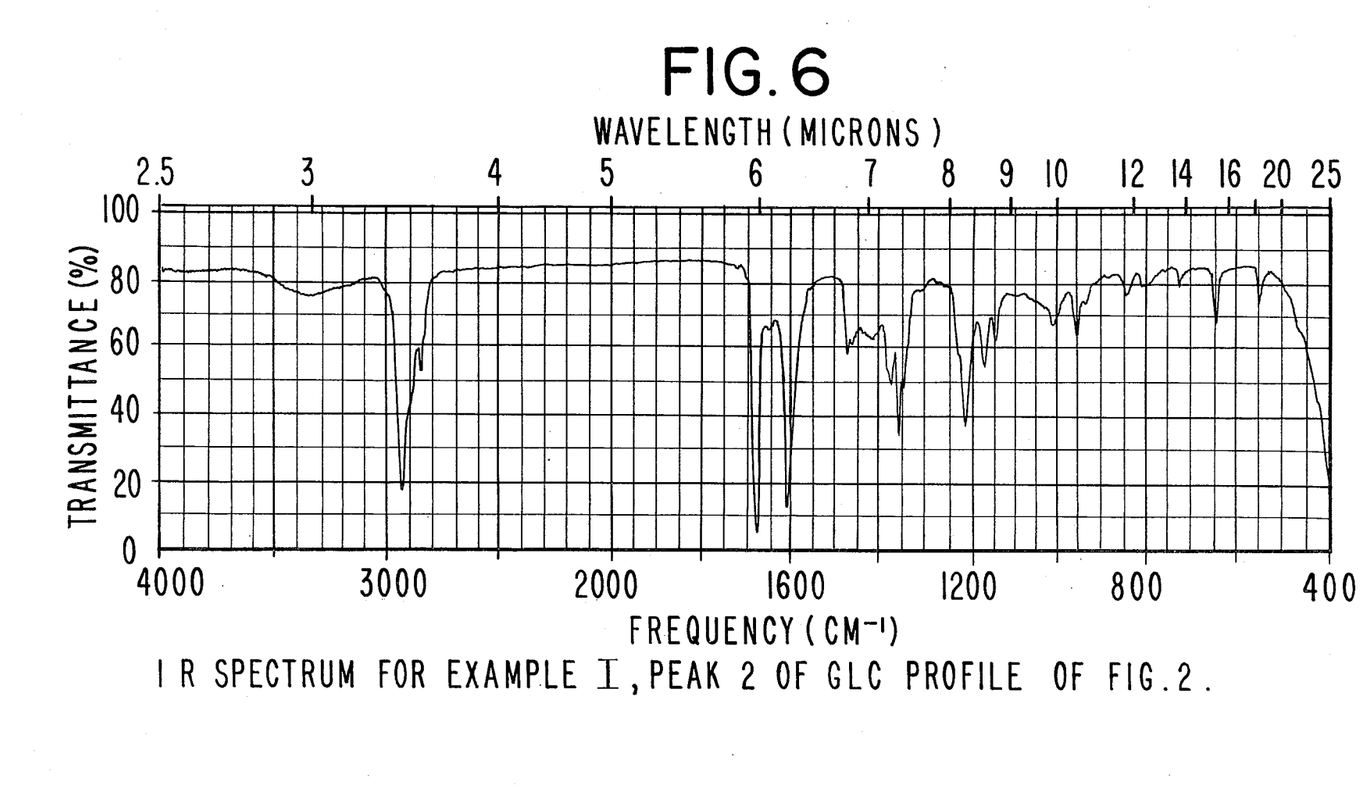
FIG. 6 is the infra-red spectrum for peak 2 of the GLC profile of FIG. 2 containing the compounds having the structures.

FIG. 6 is the infra-red spectrum for peak 2 of the GLC profile of FIG. 2 containing the compounds having the structures:

and

EXAMPLE II

Dill Spice Flavor

The following formulation is produced:

| Ingredients | Parts by Weight |
|---|---|
| Oil of dillweed | 84.5 |
| Oil of garlic | 1.75 |
| Oil of capsicum | 3.75 |
| Oil of cassia | 2.50 |
| Oil of cloves | 2.50 |
| Oil of pimenta berries | 2.50 |
| Oil of mustard | 1.25 |
| Oil of bay leaves | 1.25 |
| L-carvone | 4.60 |
| D-carvone | 3.80 |
| Cumin aldehyde | 2.51 |

The formulation is split into two parts. To one part is added the acetyl diisobutylene mixture produced according to Example I. To the second part nothing is added. Both formulations are prepared at levels of 5 ppm, 10 ppm and 20 ppm in water and in tomato ketchup. The formulation containing the acetyl diisobutylene produced according to Example I causes the flavor to be much more full-bodied and more natural-like as the flavor has caraway and minty nuances in addition to "natural" dill-like nuances. The "natural" aspect of this flavor together with the caraway-like and minty nuances are missing in the flavor that does not contain the acetyl diisobutylene composition of matter produced according to Example I.

EXAMPLE III

Spearmint Flavor

The following spearmint flavor is produced.

| Ingredients | Parts by Weight |
|---|---|
| Spearmint oil | 42.0 |
| L-carvone | 12.0 |
| D-carvone | 8.0 |

This formulation is split into two portions. To the first portion, 4.0 parts by weight of the acetyl diisobutylene produced according to Example I is added. To the second portion nothing is added. The flavor is tested at levels of 5 ppm, 10 ppm and 20 ppm in water and in chewing gum which heretofore was unflavored. The chewing gum containing the flavor formulation with the acetyl diisobutylene material produced according to Example I has a more natural-like, minty aroma and taste with excellent caraway-like and dill-like nuances present. The formulation has a great amount of "natural mintyness" which is not only "natural-like" but which is also "long lasting" and remains of high strength throughout the chewing procedure of the chewing gum.

EXAMPLE IV

A toothpaste is prepared according to the following formula:

| Ingredients | Parts by Weight |
|---|---|
| Sorbitol (70% soln.) | 20.00 |
| Sodium saccharin | 0.21 |
| Veegum (collidal magnesium aluminum silicate) | 0.40 |
| Precipitated urea/formaldehyde condensate (abrasive) | 30.00 |
| Acetyl diisobutylene prepared according to Example I, Fraction 9 of distillate | 1.00 |
| Sodium carboxymethycellulose | 1.30 |

-continued

| Ingredients | Parts by Weight |
| --- | --- |
| Glycerine | 10.00 |
| 1.2-bis($N^5$-p-chlorophenyl-$N^1$-biguanido) ethane digluconate | 0.70 |
| Polyoxyethylene sorbitan (20) monoisostearate | 1.50 |
| Distilled water | balance to 100 |

This toothpaste when used in the normal manner, is not only effective in retarding the formation of dental plaque and produces an appreciably lower level of stain on the teeth than does chlorhexidine; but, in addition, has an excellent sweet, spicy, minty, herbaceous, bread-like, caraway-like and dill-like taste profile.

EXAMPLE V

A mouthwash in accordance with the present invention is formulated as follows:

| Ingredients | Parts by Weight |
| --- | --- |
| Ethyl alcohol (95% in water) | 12.00 |
| Cetyl pyridinium chloride | 0.10 |
| Polyoxyethylene (20) sorbitan monooleate | 0.12 |
| Sodium hydroxide (10% in water) | 0.02 |
| Sodium saccharin | 0.055 |
| Acetyl diisobutylene product produced according to Example I; Fraction 2 | 0.16 |
| 1,2-bis($N^5$-p-chlorophenyl-$N^1$-biguanido) ethane dihydrochloride | 0.20 |
| Color | 0.50 |
| Sorbitol (70% in water) | 12.00 |
| Distilled water | balance to 100 |

When used in the normal manner to rinse the mouth, this product is effective not only in retarding the formation of dental plaque and produces an appreciably lower level of stain on the teeth than does chlorohexidine; but it also has an excellent sweet, spicy, minty, herbaceous, bread-like, caraway-like, and dill-like taste profile.

EXAMPLE VI

A chewing gum in accordance with the present invention is formulated as follows:

| Ingredients | Parts by Weight |
| --- | --- |
| Gum base | 21.30 |
| Ester Gum | 6.40 |
| Coumarone resin | 9.60 |
| Dry latex rubber | 3.20 |
| Paraffin wax (M.P. 180° F.) | 2.10 |
| Sugar | 58.45 |
| Corn syrup (Baume 45) | 18.20 |
| Acetyl diisobutylene product produced according to Example I; bulked Fractions 2-9 | 1.05 |
| 1,2-bis($N^5$-p-chlorophenyl-$N^1$-biguanido) ethane diacetate | 1.00 |

Chewing this gum in the normal manner not only retards the formation of dental plaque and produces appreciably less staining on the teeth than does chlorhexidine but it also gives rise to a pleasant, long-lasting and intense sweet, spicy, minty, herbaceous, bread-like, caraway-like and dill-like taste profile.

What is claimed is:

1. A process for augmenting or enhancing the aroma or taste of a consumable material selected from the group consisting of foodstuffs, chewing gums, toothpastes and mouthwashes, comprising the steps of adding to said consumable material from 0.02 ppm up to about 50 ppm based on total weight of said consumable material of a composition of matter containing a major proportion of acetyl diisobutylene molecules defined according to the structure:

wherein in the mixture, in each of the molecules, one of the dashed lines represents a carbon-carbon double bond and the other of the dashed lines represents a carbon-carbon single bond produced according to the process comprising the steps of (a) dimerizing isobutylene in the presence of an alkyl aluminum chloride catalyst thereby producing a mixture of dimers and (b) acylating the resulting mixture of dimers with an acetylating agent selected from the group consisting of acetic anhydride, acetyl chloride and acetyl bromide in the presence of a catalyst selected from the group consisting of boron trifluoride, boron trifluoride etherate, stannic chloride, ethyl aluminum dichloride and diethyl aluminum chloride and distilling the resultant reaction product at a vapor temperature in the range of 50°-53° C. and a liquid temperature in the range of 59°-65° C. and a pressure of 2.0 mm/Hg.

2. The process of claim 1 wherein the consumable material is a foodstuff.

3. The process of claim 1 wherein the consumable material is a toothpaste.

4. The process of claim 1 wherein the consumable material is a mouthwash.

5. The process of claim 1 wherein the consumable material is a chewing gum.

6. A chewing gum composition comprising a bisbiguanide compound and a composition of matter comprising a major proportion of a mixture of compounds defined according to the structure:

wherein in each of the molecules of the mixture, one of the dashed lines is a carbon-carbon double bond and each of the other of the dashed lines is a carbon-carbon single bond, produced according to the process comprising the steps of (a) dimerizing isobutylene in the presence of an alkyl aluminum chloride catalyst thereby producing a mixture of dimers and (b) acylating the resulting mixture of dimers with an acetylating agent selected from the group consisting of acetic anhydride, acetyl chloride and acetyl bromide in the presence of a catalyst selected from the group consisting of boron trifluoride, boron trifluoride etherate, stannic chloride, ethyl aluminum dichloride and diethyl aluminum chloride and distilling the resultant reaction product at a vapor temperature in the range of 50°-53° C. and a liquid temperature in the range of 59°-65° C. and a pressure of 2.0 mm/Hg, said composition of matter being in a concentration sufficient to impart a sweet, spicy, minty, herbaceous, bread-like, caraway-like and dill-like taste profile.

7. The chewing gum of claim 6 wherein the acetyl diisobutylene containing product-by-process is in the chewing gum in a concentration of from 0.02 parts per million up to about 50 parts per million.

* * * * *